United States Patent [19]

Ridland et al.

[11] Patent Number: 5,866,710
[45] Date of Patent: Feb. 2, 1999

[54] ESTERIFICATION PROCESS

[75] Inventors: John Ridland, Durham; Iain Wesley Hepplewhite, Hartlepool; Brian Steven Jolly, Ruislip, all of England

[73] Assignee: Tioxide Specialties Limited, London, England

[21] Appl. No.: 869,629

[22] Filed: Jun. 5, 1997

[30] Foreign Application Priority Data

Jun. 11, 1996 [GB] United Kingdom .................. 9612161

[51] Int. Cl.$^6$ .................................................. C07C 67/08
[52] U.S. Cl. ............................. 560/98; 560/56; 560/67; 560/180; 560/204; 560/231; 554/170
[58] Field of Search .............................. 560/98, 231, 67, 560/56, 204, 180; 554/170

[56] References Cited

U.S. PATENT DOCUMENTS

| | | |
|---|---|---|
| 3,047,515 | 7/1962 | Piirma . |
| 4,452,969 | 6/1984 | McCready . |
| 4,780,527 | 10/1988 | Tong et al. . |

FOREIGN PATENT DOCUMENTS

| | | |
|---|---|---|
| 48-034 132 | 5/1973 | Japan . |
| 53-098 393 | 8/1978 | Japan . |
| 7-207 010 | 8/1995 | Japan . |
| 811 425 | 4/1958 | United Kingdom . |
| 851 600 | 10/1960 | United Kingdom . |
| 970 431 | 9/1964 | United Kingdom . |
| 988 626 | 4/1965 | United Kingdom . |
| 991 020 | 5/1965 | United Kingdom . |
| 1 514 361 | 6/1978 | United Kingdom . |
| 2 207 426 | 2/1989 | United Kingdom . |
| 2 207 434 | 2/1989 | United Kingdom . |

*Primary Examiner*—Samuel Barts

[57] ABSTRACT

A process for the preparation of an ester comprises carrying out an esterification in the presence of a catalyst comprising the reaction product of an orthoester or a condensed orthoester of titanium or zirconium, an alcohol containing at least two hydroxyl groups, a 2-hydroxy acid and a base. The process can be a direct esterification or a transesterification and can be a polyesterification. The catalyst can effectively produce esters without leading to a haze in the final product and there is a reduced amount of yellowing of polyesters in comparison to known catalysts.

20 Claims, No Drawings

ESTERIFICATION PROCESS

The invention concerns an esterification process and in particular an esterification process which utilises a novel organotitanium or organozirconium catalyst.

Organotitanium compounds and, in particular, titanium alkoxides or orthoesters are known as catalysts for esterification processes. During the esterification, these compounds are frequently converted to polymeric compounds of titanium which result in a hazy product. The presence of a haze is a particular disadvantage in polyesters which have a high viscosity and/or high melting point and are therefore difficult to filter. Furthermore, many organotitanium compounds which are effective catalysts in the manufacture of polyesters such as polyethylene terephthalate are known to produce unacceptable yellowing in the final polymer.

It is an object of the present invention to provide an improved process for preparing esters.

According to the invention, a process for the preparation of an ester comprises carrying out an esterification reaction in the presence of a catalyst comprising the reaction product of an orthoester or condensed orthoester of titanium or zirconium, an alcohol containing at least two hydroxyl groups, a 2-hydroxy carboxylic acid and a base.

The esterification reaction of the process of the invention can be any reaction by which an ester is produced. The reaction may be a direct esterification in which a carboxylic acid or its anhydride and an alcohol react to form an ester or a transesterification (alcoholysis) in which a first alcohol reacts with a first ester to produce an ester of the first alcohol and a second alcohol produced by cleavage of the first ester or a transesterification reaction in which two esters are reacted to form two different esters by exchange of alkoxy radicals. Direct esterification or transesterification can be used in the production of polymeric esters and a preferred process of the invention comprises a polyesterification process.

Many carboxylic acids and anhydrides can be used in direct esterification including saturated and unsaturated monocarboxylic acids such as stearic acid, isostearic acid, capric acid, caproic acid, palmitic acid, oleic acid, palmitoleic acid, triacontanoic acid, benzoic acid, methyl benzoic acid and salicylic acid, dicarboxylic acids such as phthalic acid, isophthalic acid, terephthalic acid, sebacic acid, adipic acid, azelaic acid, succinic acid, fumaric acid, maleic acid, naphthalene dicarboxylic acid and pamoic acid and anhydrides of these acids and polycarboxylic acids such as trimellitic acid, citric acid, trimesic acid, pyromellitic acid and anhydrides of these acids. Alcohols frequently used for direct esterification include aliphatic straight chain and branched monohydric alcohols such as butyl, pentyl, hexyl, octyl and stearyl alcohols and polyhydric alcohols such as glycerol and pentaerythritol. A particularly preferred process of the invention comprises reacting 2-ethylhexanol with phthalic anhydride to form bis(2-ethylhexyl)phthalate.

The esters employed in an alcoholysis reaction are generally the lower homologues such as methyl, ethyl and propyl esters since, during the esterification reaction, it is usual to eliminate the displaced alcohol by distillation. Such esters of the acids suitable for direct esterification are used in the process of the invention. Frequently (meth)acrylate esters of longer chain alcohols are produced by alcoholysis of esters such a methyl acrylate, methyl methacrylate, ethyl acrylate and ethyl methacrylate. Typical alcohols used in alcoholysis reactions include butyl, hexyl, n-octyl and 2-ethyl hexyl alcohols and substituted alcohols such as dimethylaminoethanol.

When the esterification reaction is a transesterification between two esters, generally the esters will be selected so as to produce a volatile product ester which can be removed by distillation.

As mentioned hereinbefore, polymeric esters can be produced by processes involving direct esterification or transesterification and a particularly preferred embodiment of the process of the invention is a polyesterification reaction in the presence of the catalyst described hereinbefore. In a polyesterification reaction polybasic acids or esters of polybasic acids are usually reacted with polyhydric alcohols to produce a polymeric ester. Linear polyesters are produced from dibasic acids such as those mentioned hereinbefore or esters of said dibasic acids and dihydric alcohols. Preferred polyesterification reactions according to the invention include the reaction of terephthalic acid or dimethyl terephthalate with 1,2-ethanediol (ethylene glycol) to produce polyethylene terephthalate or with 1,4-butanediol (butylene glycol) to produce polybutylene terephthalate or reaction of naphthalene dicarboxylic acid with 1,2-ethanediol to produce polyethylene naphthalenate. Other glycols such as 1,3-propanediol, 1,6-hexanediol, trimethylpropane and pentaerythritol are also suitable for preparing polyesters.

A typical process for the preparation of polyethylene terephthalate comprises two stages. In the first stage terephthalic acid or dimethyl terephthalate is reacted with 1,2-ethanediol to form a prepolymer and the by-product water or methanol is removed. The prepolymer is subsequently heated in a second stage to remove 1,2-ethanediol and form a long chain polymer. Either or both these stages may comprise a process according to this invention.

The catalyst which is used in the process of the invention is the reaction product of a titanium or zirconium orthoester or condensed orthoester, an alcohol containing at least two hydroxyl groups, a 2-hydroxy carboxylic acid and a base. Preferably, the orthoester has the formula $M(OR)_4$ in which M is titanium or zirconium and R is an alkyl group. More preferably R contains 1 to 6 carbon atoms and particularly suitable orthoesters include tetraisopropoxy titanium, tetra-n-butoxy titanium, tetra-n-propoxy zirconium and tetra-n-butoxy zirconium.

The condensed orthoesters suitable for preparing the catalysts useful in this invention are typically prepared by careful hydrolysis of titanium or zirconium orthoesters and are frequently represented by the formula $$R^1O[M(OR^1)_2O]_nR^1$$

in which $R^1$ represents an alkyl group and M represents titanium or zirconium. Preferably, n is less than 20 and more preferably is less than 10. Preferably $R^1$ contains 1 to 6 carbon atoms and useful condensed orthoesters include the compounds known as polybutyl titanate, polyisopropyl titanate and polybutyl zirconate.

Preferably the alcohol containing at least two hydroxyl groups is a dihydric alcohol and can be a 1,2-diol such as 1,2-ethanediol, 1,2-propanediol, a 1,3-diol such as 1,3-propanediol or a dihydric alcohol containing a longer chain such as diethylene glycol or a polyethylene glycol. Preferred dihydric alcohols are 1,2-ethanediol and diethylene glycol. The catalyst can also be prepared from a polyhydric alcohol such as glycerol, trimethylolpropane or pentaerythritol.

Preferably the catalyst is prepared by reacting a dihydric alcohol with an orthoester or condensed orthoester in a ratio of from 2 to 12 moles of dihydric alcohol to each mole of the titanium or zirconium. More preferably the reaction product contains 4 to 8 moles dihydric alcohol per mole of titanium or zirconium.

Preferred 2-hydroxy carboxylic acids include lactic acid, citric acid malic acid and tartaric acid. Some suitable acids are supplied as hydrates or as aqueous mixtures. Acids in this form as well as anhydrous acids are suitable for preparing the catalysts used in this invention. The preferred molar ratio of acid to titanium or zirconium in the reaction product is 1 to 4 moles per mole of titanium or zirconium. More preferably the catalyst contains 1.5 to 3.5 moles of 2-hydroxy acid per mole of titanium or zirconium.

A base is also used in preparing the reaction product which is used as a catalyst in the process of the invention. The base is generally an inorganic base and suitable bases include sodium hydroxide, potassium hydroxide, ammonium hydroxide, sodium carbonate, magnesium hydroxide and ammonia. Frequently, the amount of base used is sufficient to fully neutralise the 2-hydroxy carboxylic acid but it is not essential that the acid is fully neutralised. Therefore, for monobasic 2-hydroxy acids such as lactic acid, the preferred amount of base is in the range 0.8 to 1.2 mole per mole of 2-hydroxy acid. In the case of citric acid (a tribasic acid), the preferred amount is in the range 1 to 3 moles base per mole of 2-hydroxy acid. In general, the amount of base present is usually in the range 1 to 12 moles per mole of titanium or zirconium and preferably the amount of base is from 1 to 4 moles per mole of titanium or zirconium.

Typically, the catalysts of the invention are neutral. It is frequently convenient to add water together with the base when preparing the catalysts. Frequently, products which contain water have a pH in the range 6 to 8.

The catalyst can be prepared by mixing the components (orthoester or condensed orthoester, dihydric alcohol, 2-hydroxy acid and base) with removal of any by-product, (e.g. isopropyl alcohol when the orthoester is tetraisopropoxytitanium), at any appropriate stage. In one preferred method the orthoester or condensed orthoester and dihydric alcohol are mixed and subsequently, 2-hydroxy acid and then base are added or a preneutralised 2-hydroxy acid solution, is added. In an alternative preferred method the orthoester or condensed orthoester is reacted with the 2-hydroxy acid and by-product alcohol is removed. Base is then added to this reaction product followed by a dihydric alcohol to produce the reaction product which is a catalyst in the process of the invention. If desired, further by-product alcohol can then be removed by distillation.

The esterification reaction of the invention can be carried out using any appropriate, known technique for an esterification reaction.

In direct esterification the acid or anhydride and an excess of alcohol are typically heated, if necessary in a solvent, in the presence of the catalyst. Water is usually the by-product of the reaction and this is removed, as an azeotrope with a boiling mixture of solvent and/or alcohol. Generally, the solvent and/or alcohol mixture which is condensed is immiscible with water which is therefore separated before solvent and/or alcohol are returned to the reaction vessel. When reaction is complete the excess alcohol and, when used, solvent are evaporated. In contrast to prior art esterification processes, it is not generally necessary to remove the catalyst from the reaction mixture. A typical direct esterification reaction is the preparation of bis(2-ethylhexyl) phthalate which is prepared by mixing phthalic anhydride and 2-ethyl hexanol. An initial reaction to form a monoester is fast but the subsequent conversion of the monoester to diester is carried out by refluxing in the presence of the catalyst at a temperature of 180°–200° C. until all the water has been removed. Subsequently the excess alcohol is removed.

In an alcoholysis reaction, the ester, first alcohol and catalyst are mixed and, generally, the product alcohol (second alcohol) is removed by distillation often as an azeotrope with the ester. Frequently it is necessary to fractionate the vapour mixture produced from the alcoholysis in order to ensure that the second alcohol is separated effectively without significant loss of product ester or first alcohol. The conditions under which alcoholysis reactions are carried out depend principally upon the components of the reaction and generally components are heated to the boiling point of the mixture used.

A preferred process of the invention is the preparation of polyethylene terephthalate. A typical batch production of polyethylene terephthalate is carried out by charging terephthalic acid and ethylene glycol to a reactor along with catalyst if desired and heating the contents to 260°–270° C. under a pressure of about 0.3 MPa. Reaction commences as the acid dissolves at about 230° C. and water is removed. The product is transferred to a second autoclave reactor and catalyst is added, if needed. The reactor is heated to 290°–300° C. under an eventual vacuum of 100 Pa to remove ethylene glycol by-product. The molten product ester is discharged from the reactor, cooled and chipped.

The amount of catalyst used in the process of the invention generally depends upon the titanium or zirconium content, expressed as Ti or Zr, of the catalyst. Usually the amount is from 30 to 1000 parts per million (ppm) on weight of product ester for direct or transesterification reactions. Preferably the amount is from 30 to 450 ppm on weight of product ester and more preferably 50 to 450 ppm on weight of product ester. In polyesterification reactions the amount used is generally expressed as a proportion of the weight of product polyester and is usually from 5 to 500 ppm expressed as Ti or Zr based on product polyester. Preferably the amount is from 5 to 100 ppm expressed as Ti or Zr.

The process of this invention has been shown to effectively produce esters and polyesters at an economical rate without leading to haze in the final product and with a reduced amount of yellowing of polyesters in comparison to known catalysts.

The invention is illustrated by the following examples.

PREPARATION OF CATALYSTS

EXAMPLE 1

Ethylene glycol (217.85 g, 3.51 moles) was added from a dropping funnel to stirred titanium isopropoxide (284.8, 1.00 moles) in a 1 liter fishbowl flask fitted with stirrer, condenser and thermometer. The rate of addition was controlled so that the heat of reaction caused the contents of the flask to warm to about 50° C. The reaction mixture was stirred for 15 minutes and aqueous 85% wt/wt ammonium lactate (251.98 g, 2.00 moles) was added to the reaction flask to yield a clear, pale yellow liquid (Ti content 6.54% by weight).

EXAMPLE 2

Following the method of Example 1, ethylene glycol (496.37 g, 8.0 moles) was added to titanium isopropoxide (284.8 g, 1.0 mole) followed by reaction with aqueous 60% wt/wt sodium lactate (374.48 g, 2.0 moles) to yield a pale yellow liquid. (Ti content 4.13% by weight).

EXAMPLE 3

To titanium isopropoxide (142.50 g, 0.50 moles) in a 1 liter conical flask, fitted with sidearm condenser, supported on and stirred by means of a magnetic stirrer was slowly added ethylene glycol (248.25 g, 4.0 moles) from a dropping funnel. When addition was complete the contents were stirred for 15 minutes before adding aqueous 60% wt/wt potassium lactate (213.03 g, 1.0 mole) by dropping funnel to yield a clear, very pale yellow product (Ti content 3.91% by weight).

EXAMPLE 4

Following the method of example 3, diethylene glycol (127.58 g, 1.20 moles) was added to 135.95 g (0.3 moles) zirconium n-propoxide (72.3% wt/wt in n-propanol). To this stirred product was added aqueous 60% wt/wt sodium lactate (112.04 g, 0.60 moles) to yield a pale yellow product (Zr content 7.28% by weight).

EXAMPLE 5

Citric acid monohydrate (132.5 g, 0.63 moles) was dissolved in warm water (92.8 g) in a 1 liter fishbowl flask fitted with stirrer, condenser and thermometer. To the stirred solution was added slowly titanium isopropoxide (72.0 g, 0.25 moles) from a dropping funnel. This mixture was heated to reflux for 1 hour to yield a hazy solution from which isopropanol/water mixture was distilled under vacuum. The product was cooled to below 70° C. and 32% wt/wt aqueous NaOH (94.86 g, 0.76 moles) was added slowly by dropping funnel to the stirred solution. The resultant product was filtered, then mixed with ethylene glycol (125.54 g, 2.0 moles) and heated under vacuum to remove isopropanol/water and yield a slightly hazy pale yellow product (Ti content 3.85% by weight).

The sensitivity of the product of Example 5 to reaction with colour-forming species was tested by mixing the catalyst with a dilute solution of diethyldihydroxy terephthalate in toluene (0.04 g/ml). The colour of the resultant solution was measured on a LICO 200 spectrophotometer in an 11 mm cylindrical glass cuvette and compared with a solution containing tetraisopropoxy titanium [$Ti(O^iPr)_4$]. Results are shown below.

| Catalyst | Metal added (mmol) | Solution Colour (Gardner Units) |
|---|---|---|
| None | 0 | 4.7 |
| $Ti(O^iPr)_4$ | 1.4 | 11.9 |
| Example 5 | 1.4 | 4.7 |

ESTERIFICATION

EXAMPLE 6

The products of examples 3, 4 and 5 were tested at equivalent metal (Ti or Zr) level as catalysts for the preparation of bis(2-ethylhexyl phthalate). Titanium tetraisopropoxide ($Ti(O^iPr)_4$) was used as a comparative catalyst.

The apparatus was a 1-liter, 4-necked round-bottomed flask fitted with a thermometer, rubber seal, a tube dipping below the surface of the reactants and a Dean and Stark apparatus. The equipment was operated under reduced pressure using an oil vacuum pump connected to two water condensers fitted above the Dean and Stark apparatus. The dip tube in the flask was connected to a supply of oxygen-free nitrogen. This provided a nitrogen bleed to aid the removal of water during the reaction.

1.0 mole (148 g) phthalic anhydride was added to 2.42 moles (315 g) 2-ethylhexanol. The mixture was heated to dissolve the phthalic anhydride and the nitrogen flow started.

When the temperature had reached 180° C. a weighed amount of catalyst was added via the rubber seal with a syringe, below the surface of the reactants. The reaction mixture was maintained at a vigorous reflux at 200° C. by suitable adjustment of the heating rate and vacuum. The water produced was removed substantially as quickly as it was formed and collected in the Dean and Stark apparatus.

The progress of the reaction was followed by withdrawing samples at intervals by means of a syringe fitted with a 30 cm needle inserted through the rubber seal. Each sample was added to a known weight (approximately 100 g) of cold alcohol to quench the reaction, weighed and titrated against standard potassium hydroxide solution in ethanol using bromophenol blue as indicator. The results were used to calculate the amount of unreacted half-ester present.

The reaction was continued for a total of 160 minutes.

The results are given below:

| Catalyst | ppm Metal[1] | Product Colour[2] | Product Clarity | % Conversion |
|---|---|---|---|---|
| $Ti(O^iPr)_4$[3] | 172 | 85 | Hazy | 99.9 |
| Example 3 | 171 | 85 | Hazy | 99.6 |
| Example 4 | 170 | 15 | Clear | 85.4 |
| Example 5 | 167 | 60 | Clear | 98.3 |

[1]Wt. of Zr or Ti based on weight of ester in parts per million
[2]Hazen units. Colour of final reaction ixture.
[3]The $Ti(O^iPr)_4$ catalyst was added as a 10 ml solution in 2-ethyl hexanol.
[4]After a reaction time of 160 minutes.

1. Wt. of Zr or Ti based on weight of ester in parts per million
2. Hazen units. Colour of final reaction mixture.
3. The $Ti(O^iPr)_4$ catalyst was added as a 10 ml solution in 2-ethyl hexanol.
4. After a reaction time of 160 minutes.

EXAMPLE 7

The products of examples 3, 4 and 5 were used to prepare polyethylene terephthalate (PET). Ethylene glycol (26 liters) and terephthalic acid (60.5 kg) were charged to a jacketed reactor. The catalyst and other additives were added and the reactor heated to 226°–252° C. to initiate the first stage direct esterification (DE) process. On completion of the DE reaction the contents of the reactor were transferred to a stirred autoclave. Stabilisers and catalyst ($Sb_2O_3$) were added and the mixture heated to 290°±2° C. under vacuum to remove ethylene glycol and yield polyethylene terephthalate. The batch details were as follows.

| 1st Stage (DE) Catalyst | ppm Metal[1] | 1st Stage Time (min) | 2nd Stage Time (min) | Product Colour[2] | Product Clarity |
|---|---|---|---|---|---|
| $Ti(O^iPr)_4$ | 42 | 100 | 77 | −2.80 | Hazy |
| Example 3 | 30 | 65 | 76 | 0.4 | Sl. Haze |
| Example 4 | 36 | 91 | 73 | 1.2 | Sl. Haze |
| Example 5 | 25 | 72 | 74 | 2.3 | Clear |

[1]Weight of Zr or Ti based on final weight PET in parts per million
[2]b-values (yellowing) on the CIE $L_h$, $a_h$ and $b_h$ scale 1. Weight Zr or Ti based on final weight PET in parts per million
2. b-values (yellowing) on the CIE $L_h$, $a_h$ and $b_h$ scale

EXAMPLE 8

Phosphate stabilisers are frequently added to polyesterification reactions but they are known to at least partly deactivate titanium catalysts. The following example demonstrates that the catalysts used in this invention are more resistant to deactivation than conventional catalyst such as tetraisopropoxy titanium.

Example 6 was repeated except that phosphoric acid was added to the reaction mixture prior to addition of the catalyst.

Results are given below.

| Catalyst | ppm Ti[1] | ppm Phosphorus[2] | % Conversion[3] |
|---|---|---|---|
| Ti(O$^i$Pr)$_4$ | 178 | 90 | 90.60 |
| Example 5 | 178 | 101 | 96.40 |
| Example 5 | 177 | 83 | 97.04 |
| Example 3 | 177 | 79 | 96.23 |

[1]Weight of Ti based on weight of ester
[2]Weight of P based on weight of ester
[3]After a reaction time of 160 minutes.

1. Weight of Ti based on weight of ester
2. Weight of P based on weight of ester
3. After a reaction time of 160 minutes.

EXAMPLE 9

The product of Example 5 was used to prepare polyethylene terephthalate using a batch terephthalic acid based route. The esterification vessel was charged with 2250 kg terephthalic acid and 1050 liters of ethylene glycol, 50 ppm NaOH and 1920 ppm of a solution of the catalyst of Example 5 (80 ppm Ti atoms, based on potential polyester). The mixture was heated to 265° C. until all the water produced had been distilled off. 155 ppm phosphoric acid stabiliser was then added and the reaction mixture was transferred to an autoclave.

300 ppm cobalt acetate tetrahydrate was added, the reaction mixture was heated to 295° C. and polymerisation under vacuum occurred. The final polyester had an intrinsic viscosity of 0.685 (as measured by solution viscosity on an 8% solution of the polyester in o-chlorophenol at 25° C.), was glass clear and showed no signs of catalyst haze.

A molten web of the polyester prepared above was extruded in conventional manner from a die on to the polished surface of a cooled rotating drum upon which the web was quenched to below the glass transition temperature of the polyester to provide an amorphous film. The quenched film was then reheated and drawn to about 3.2 times its original length in the machine direction, passed into a stenter oven and the sheet stretched in the transverse direction, to approximately 3.8 times its original dimensions, followed by heat setting. Final thickness was 125 micrometer. The wide angle haze of the film was 0.5 1%.

When the above preparation was repeated using 250 ppm of tetraisoproxy titanium (40 ppm Ti atoms), a conventional catalyst, in place of the catalyst of Example 5 the wide angle haze of the resultant film was 1.35%.

EXAMPLE 10

The product of Example 5 was used to prepare polyethylene terephthalate using the melt polymerisation process described in Example 9. The resultant polymer had an intrinsic viscosity of 0.685 (as measured by solution viscosity on an 8% solution of the polyester in o-chlorophenol at 25° C.), was transparent and showed no signs of catalyst haze.

750 g of the polymer prepared above was then polymerised in the solid state at 213° C. under a flow of nitrogen to yield a polyethylene terephthalate polymer having an intrinsic viscosity of 0.82 measured by melt viscometry. The rate of solid state polymerisation using the catalyst of Example 5 was significantly faster than that achieved using a standard antimony trioxide catalyst. The rate of intrinsic viscosity increase (indicative of polymerisation rate) was 0.027 units per hour whereas with antimony trioxide the rate was 0.015 units per hour.

The final polymer was converted to bottles using an injection stretch blow moulding technique.

We claim:

1. A process for the preparation of an ester comprising carrying out an esterification reaction in the presence of a catalyst comprising the reaction product of (a) a compound selected from the group consisting of orthoesters and condensed orthoesters of a metal selected from the group consisting of titanium and zirconium, (b) an alcohol containing at least two hydroxyl groups, (c) a 2-hydroxy carboxylic acid and (d) a base.

2. A process according to claim 1 in which the orthoester has the formula M(OR)$_4$ wherein M is a metal selected from the group consisting of titanium and zirconium and R is an alkyl group containing 1 to 6 carbon atoms.

3. A process according to claim 1 in which the condensed orthoester has the formula R$^1$O[M(OR$^1$)$_2$O]$_n$R$^1$ wherein R$^1$ is an alkyl group containing 1 to 6 carbon atoms and M is a metal selected from the group consisting of titanium and zirconium.

4. A process according to claim 3 in which n is less than 20.

5. A process according to claim 1 in which the alcohol containing at least two hydroxyl groups is a dihydric alcohol.

6. A process according to claim 5 in which the catalyst contains from 2 to 12 moles of dihydric alcohol per mole of titanium or zirconium.

7. A process according to claim 1 in which the 2-hydroxy acid is selected from the group consisting of lactic acid, citric acid, malic acid and tartaric acid.

8. A process according to claim 1 in which the catalyst contains from 1 to 4 moles of 2-hydroxy acid per mole of titanium or zirconium.

9. A process according to claim 1 in which the base is selected from the group consisting of sodium hydroxide, potassium hydroxide, ammonium hydroxide, sodium carbonate, magnesium hydroxide and ammonia.

10. A process according to claim 1 in which the catalyst is prepared from a monobasic 2-hydroxy carboxylic acid and in which the base is used in an amount in the range 0.8 to 1.2 mole of base per mole of 2-hydroxy carboxylic acid.

11. A process according to claim 1 in which the catalyst is prepared from a tribasic 2-hydroxy carboxylic acid and in which the base is used in an amount in the range 1 to 3 mole of base per mole of 2-hydroxy carboxylic acid.

12. A process according to claim 1 in which the catalyst contains from 1 to 12 moles of base per mole of titanium or zirconium.

13. A process according to claim 1 in which the catalyst contains water and has a pH in the range 6 to 8.

14. A process according to claim 1 in which the esterification reaction comprises reaction of an alcohol with an acid selected from the group consisting of stearic acid, isostearic acid, capric acid, caproic acid, palmitic acid, oleic acid, palmitoleic acid, triacontanoic acid, benzoic acid, methyl benzoic acid, salicylic acid, phthalic acid, isophthalic acid, terephthalic acid, sebacic acid, adipic acid, azelaic acid, succinic acid, fumaric acid, maleic acid, naphthalene dicarboxylic acid, pamoic acid, trimellitic acid, citric acid, trimesic acid and pyromellitic acid.

15. A process according to claim 1 in which the esterification reaction comprises reaction of an alcohol with the anhydride of an acid selected from the group consisting of dicarboxylic acids and tricarboxylic acids.

16. A process according to claim 1 in which the esterification reaction comprises reaction of an ester selected from the group consisting of methyl esters, ethyl esters and propyl esters of an acid selected from the group consisting of acrylic acid and methacrylic acid with an alcohol.

17. A process according to claim 1 in which the esterification reaction comprises the reaction of two esters to produce two different esters by exchange of alkoxy groups.

18. A process according to claim 1 in which the esterification reaction comprises a polyesterification comprising the reaction of a compound selected from the group consisting of terephthalic acid and dimethyl terephthalate with an alcohol selected from the group consisting of 1,2-ethanediol, 1,4-butanediol, 2,3-propanediol, 1,6-hexanediol, trimethylol-propane and pentaerythritol.

19. A process according to claim 1 in which the esterification reaction is a direct esterification or a transesterification and the catalyst is present in an amount in the range 30 to 1000 parts per million calculated as parts by weight of titanium or zirconium with respect to weight of product ester.

20. A process according to claim 1 in which the esterification is a polyesterification and the catalyst is present in an amount in the range 5 to 500 parts per million calculated as parts by weight titanium or zirconium with respect to weight of product polyester.

* * * * *